US010806858B2

(12) United States Patent
Lee et al.

(10) Patent No.: US 10,806,858 B2
(45) Date of Patent: Oct. 20, 2020

(54) AUTOMATIC ANESTHESIOLOGY PUMP ALLOWING IMPROVED ANESTHESIOLOGIST MOBILITY

(71) Applicant: Zyno Medical, LLC, Natick, MA (US)

(72) Inventors: Chao Young Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 0 days.

(21) Appl. No.: 15/045,881

(22) Filed: Feb. 17, 2016

(65) Prior Publication Data

US 2017/0232194 A1 Aug. 17, 2017

(51) Int. Cl.
*A61M 5/172* (2006.01)
*G16H 20/17* (2018.01)
(Continued)

(52) U.S. Cl.
CPC ...... *A61M 5/1723* (2013.01); *A61M 5/14228* (2013.01); *A61M 5/16886* (2013.01); *G06F 1/163* (2013.01); *G06F 19/3468* (2013.01); *G16H 20/17* (2018.01); *G16H 40/67* (2018.01); *A61B 5/4839* (2013.01); *A61M 2005/14208* (2013.01); *A61M 2005/16863* (2013.01); *A61M 2202/048* (2013.01); *A61M 2205/18* (2013.01);
(Continued)

(58) Field of Classification Search
CPC ..... G06F 19/3468; A61M 2005/14208; A61M 2005/16863; A61M 2202/048; A61M 2205/18; A61M 2205/3553; A61M 2205/3584; A61M 2205/50; A61M 2205/502; A61M 2205/52; A61M 2205/581; A61M 2205/582; A61M 2205/583; A61M 2205/005; A61M 2205/10; A61M 2205/20; A61M 2205/42; A61M 2205/43; A61B 5/0022
See application file for complete search history.

(56) References Cited

U.S. PATENT DOCUMENTS 6,317,627 B1 11/2001 Ennen et al.
6,415,792 B1 7/2002 Schoolman
(Continued)

FOREIGN PATENT DOCUMENTS

EP 1 287 843 A2 3/2003
EP 2 410 448 A2 1/2012
(Continued)

*Primary Examiner* — Kevin C Sirmons
*Assistant Examiner* — Tezita Z Watts
(74) *Attorney, Agent, or Firm* — Boyle Fredrickson S.C.

(57) ABSTRACT

An anesthesiology pump for automatic delivery and control of anesthetics to a patient provides a remote unit that may be carried by an anesthesiologist to improve supervision of the anesthesiology process without unnecessarily constraining the anesthesiologist's movement. The anesthesiology pump may assess one or both of a status of the anesthesiology procedure and the availability of the anesthesiologist to provide tailored alerts to the anesthesiologist when additional attention or availability may be needed. Availability may consider separation distance between the pump and the radiologist as well as express indications of availability. A set of predefined safe states permit a pump response when the anesthesiologist is not available and additional attention is required.

18 Claims, 3 Drawing Sheets

(51) Int. Cl.
  *G16H 40/67* (2018.01)
  *A61M 5/142* (2006.01)
  *G06F 1/16* (2006.01)
  *A61M 5/168* (2006.01)
  *G06F 19/00* (2018.01)
  *A61B 5/00* (2006.01)

(52) U.S. Cl.
  CPC ............... *A61M 2205/3553* (2013.01); *A61M 2205/3576* (2013.01); *A61M 2205/3584* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2230/005* (2013.01); *A61M 2230/04* (2013.01); *A61M 2230/10* (2013.01); *A61M 2230/20* (2013.01); *A61M 2230/42* (2013.01); *A61M 2230/43* (2013.01)

(56) References Cited

U.S. PATENT DOCUMENTS

| | | | |
|---|---|---|---|
| 6,430,437 B1 | 8/2002 | Marro | |
| 7,347,836 B2 * | 3/2008 | Peterson | A61M 5/14228 604/65 |
| 2002/0019588 A1 | 2/2002 | Marro et al. | |
| 2002/0040208 A1 * | 4/2002 | Flaherty | A61M 5/14248 604/288.01 |
| 2006/0058700 A1 | 3/2006 | Marro et al. | |
| 2006/0093785 A1 * | 5/2006 | Hickle | A61B 5/162 428/121 |
| 2009/0124867 A1 * | 5/2009 | Hirsh | A61M 16/024 600/301 |
| 2009/0275892 A1 * | 11/2009 | Molnar | A61M 5/1723 604/116 |
| 2014/0180160 A1 | 6/2014 | Brown et al. | |
| 2014/0276549 A1 * | 9/2014 | Osorio | A61B 3/11 604/503 |
| 2014/0276587 A1 | 9/2014 | Imran | |
| 2015/0119651 A1 * | 4/2015 | Grubis | A61B 5/024 600/301 |
| 2015/0164412 A1 | 6/2015 | Kokko | |

FOREIGN PATENT DOCUMENTS

| | | |
|---|---|---|
| WO | 2013184965 A1 | 12/2013 |
| WO | 2015/100347 A2 | 7/2015 |

\* cited by examiner

AUTOMATIC ANESTHESIOLOGY PUMP ALLOWING IMPROVED ANESTHESIOLOGIST MOBILITY

CROSS-REFERENCE TO RELATED APPLICATION

Background of the Invention

The present invention relates to medical pumps for the delivery of anesthetics during medical procedures and in particular to a pump that balances independent operation with features that allow improved supervision by an anesthesiologist.

The delivery of anesthetics during medical procedures is normally supervised by a trained anesthesiologist who monitors a variety of physiological signals including blood oxygen, respiration rate, heartbeat, and brain waves in order to control the delivery of anesthetic to achieve a desired level of anesthesia. Recently, medical pumps have been developed that can perform many of these monitoring tasks and that can analyze the received data to make recommendations with respect to the adjustment of an anesthetic or actually control the anesthetic delivery. US patent application 2014/0180160 describes a system for monitoring a state of a patient during the administration of anesthetics to make recommendations with respect to drug administration. PCT patent application WO 2013184965 describes a system that monitors a patient during anesthesia to control anesthetic delivery.

For many types of anesthesiology, it is desirable to have an anesthesiologist readily available on call in the event of a problem. Requiring close supervision of such automatic anesthesiology equipment or requiring immediate availability that prevents the anesthesiologist from performing other useful tasks, however, can be an inefficient use of highly skilled personnel. Even in cases where an anesthesiologist may effectively supervise multiple automatic anesthesiology devices that are properly functioning, should an emergency occupy the anesthesiologist on one task, the assumption of immediate availability for supervision of other anesthesiology devices may no longer hold presenting a gap in procedure.

SUMMARY OF THE INVENTION

The present invention provides an automatic anesthesiology delivery device that dynamically determines a confidence level with respect to patient data and the device's delivery of anesthetic. A remote communication device carried by the anesthesiologist provides the anesthesiologist with real-time monitoring of the anesthesiology process together with tailored alerts based on this confidence level and optionally with an imputed availability of the anesthesiologist. The result is an anesthesiology delivery device that assists both in delivery of anesthetic and ensuring effective supervision by an attending anesthesiologist. In cases where there is low confidence in the delivery but the anesthesiologist cannot be available, the anesthesiology device may enter a safe state predetermined according to a particular procedure being undertaken.

In one embodiment, the invention provides a pump unit including a processor executing a program stored in non-transient media to receive physiological signals from a patient under anesthesia and to provide a controlled delivery of anesthesia to the patient in response to the received physiological signals and a remote unit communicating wirelessly with the pump unit to provide real time information to a remote anesthesiologist indicating a status of the anesthesiology procedure.

It is thus a feature of at least one embodiment of the invention to better leverage time and resources of, a trained anesthesiologist monitoring automatic anesthesiology pumps. By duplicating faceplate features of the pump on a remote device, improved supervision and anesthesiologist flexibility can be achieved.

The remote unit may be sized and may communicate with the pump unit so that it may be carried by the anesthesiologist. In one embodiment, the remote unit may include a wristband for holding on an anesthesiologist's arm in the manner of a wristwatch.

It is thus a feature of at least one embodiment of the invention to provide a remote terminal providing a high degree of mobility and also providing the ability to track the location of the anesthesiologist for accessibility purposes.

The remote unit provides a display indicating values of at least some physiological signals and/or may provide a display indicating a qualitative status of the anesthesiology procedure, for example, by a color of an icon representing the pump unit.

It is thus a feature of at least one embodiment of the invention to provide patient monitoring capabilities for the anesthesiologist as well as a quick assessment of the anesthesiology procedure.

The pump unit may process the received physiological signals to determine a confidence interval with respect to the proper anesthetics state of the patient and further provides signals to the remote unit generating alerts selected from the group of visual, audible, or tactile alerts as a predetermined change in confidence interval.

It is thus a feature of at least one embodiment of the invention to provide intelligent alerts to the anesthesiologist to minimize distractions when intervention is not required.

The remote unit may provide a display indicating a current confidence interval.

It is thus a feature of at least one embodiment of the invention to permit the anesthesiologist to readily distinguish between different types of alerts.

The pump unit may communicate with the remote unit to assess an availability of the anesthesiologist and the alerts may also be a function of the availability of the anesthesiologist.

It is thus a feature of at least one embodiment of the invention to provide a system that optimizes anesthesiologist oversight both with respect to anticipated problems and anticipated response availability.

The pump unit may determine the availability, of the anesthesiologist based on a distance between the pump unit and the anesthesiologist.

It is thus a feature of at least one embodiment of the invention to impute low availability without action by the anesthesiologist.

The assessed distance may be determined using wireless signals from the pump unit and remote unit.

It is thus a feature of at least one embodiment of the invention to make use of the same wireless communication infrastructure needed for mobility for range measurement.

The pump unit may also determine availability of the anesthesiologist at least in part by a self-reporting of availability by the anesthesiologist.

It is thus a feature of at least one embodiment of the invention to permit the anesthesiologist to indicate lack of availability, for example, so that the pump unit may seek other alternatives.

The pump unit may determine availability of the anesthesiologist at least in part by interaction by the anesthesiologist and the remote device for reviewing data on the remote device.

It is thus a feature of at least one embodiment of the invention to provide a measurement of availability that reflects engagement by the anesthesiologist such as may reduce the need for alerts.

The pump unit may provide internal diagnostics as to proper operation of the pump unit and wherein the alerts are also a function of an indication of failure of the pump unit.

It is thus a feature of at least one embodiment of the invention to use the same mechanism for anesthesiology alerts to signal equipment malfunction or risk malfunction.

These particular features and advantages may apply to only some embodiments falling within the claims and thus do not define the scope of the invention.

DETAILED DESCRIPTION OF THE PREFERRED EMBODIMENT

Figure 1:
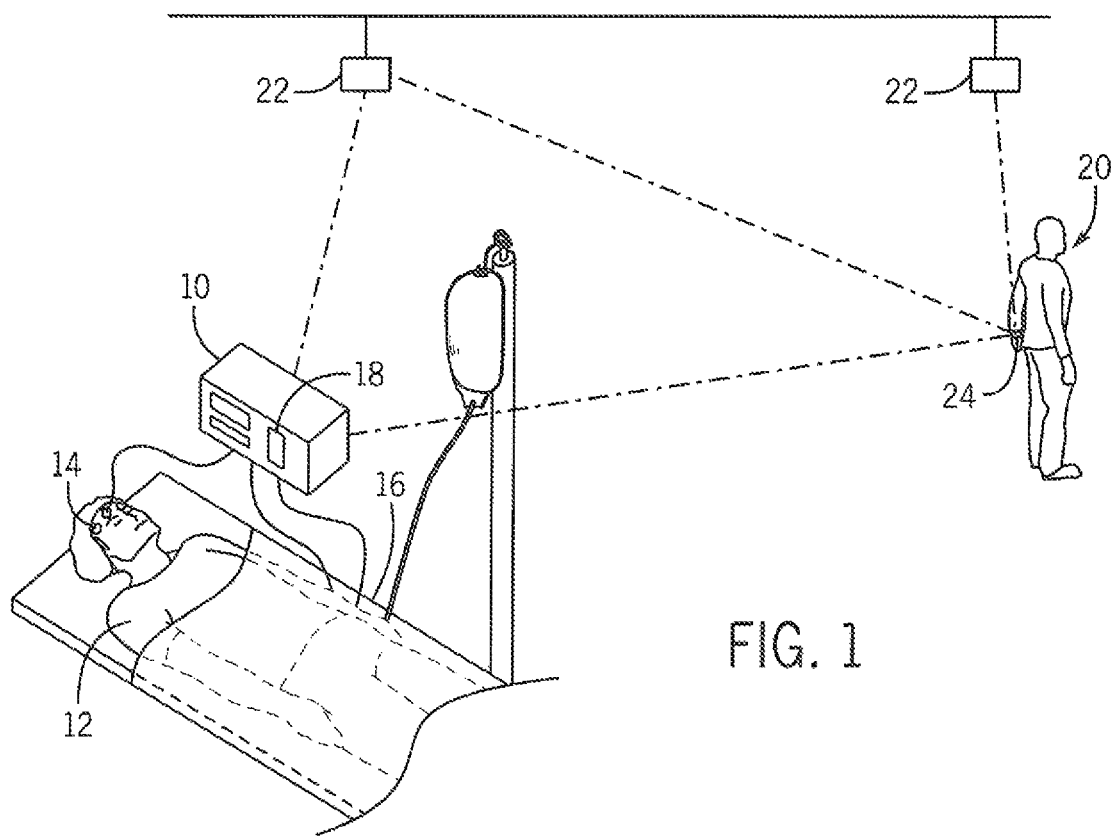
FIG. 1 is a simplified perspective view of an anesthesiology pump for monitoring, a patient and providing automatic delivery of anesthetic and further showing a system for remote communication with an anesthesiologist.

Referring now to FIG. 1, an automatic anesthetic pump 10 may be placed bedside near a patient 12 to receive physiological signals from the patient from sensors including EEG electrodes 14, a pulse blood oxygen monitor 16, and other known sensors (not shown) including optionally a respiration sensor for monitoring breathing, a capnometer for monitoring exhaled carbon dioxide, and a reaction sensor for receiving input from the patient and providing tactile output. The anesthesiology delivery device 10 may also provide an earphone 47 for communicating with the patient 12.

In operation, the automatic anesthetic pump 10 operates to deliver and anesthetic 18, for example, intravenously to the patient 12 as a function of the physiological signals from the patient 12 and internal operating rules. Examples of such systems are cited above in the background of the invention and are hereby incorporated by reference. The operating rules can be stored in the pump, or obtained remotely from a database server.

In the present invention, the automatic anesthetic pump 10 may communicate with a remote anesthesiologist 20, for example, by direct or indirect wireless communication including, for example, wireless protocols employing IEEE 801.11 or similar standards, as well as Bluetooth and the like. In one embodiment, the automatic anesthetic pump 10 provides wireless communication with one or more wireless access points 22, the latter being part of a network of wireless access points. This network of wireless access points 22 may also communicate with a mobile unit 24 held by the anesthesiologist 20.

The wireless access points 22 may provide geolocation capabilities to identify one or both of the location of the automatic anesthetic pump 10 and the location of the anesthesiologist 20, for example, by trilateralization or other known location technologies. Alternatively, the automatic anesthetic pump 10 may communicate directly with the mobile unit 24, without the need for a network of wireless access points 22, for example, by Bluetooth communication, and the Bluetooth communication channel used to determine a distance of the anesthesiologist 20 from the automatic anesthetic pump 10. This distance or location information will be used to determine the availability of the anesthesiologist 20.

Figure 2:
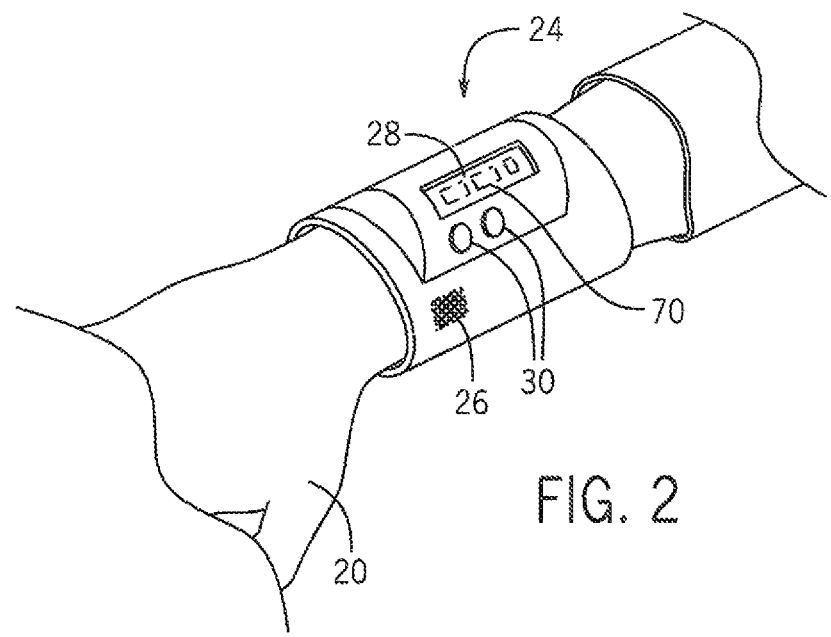
FIG. 2 is a fragmentary view of a wristband providing remote communication with the anesthesiology pump providing the anesthesiologist with both real-time data and tailored alerts to assist in monitoring one or more pumps.

Referring now to FIG. 2, in one embodiment, the mobile unit 24 may provide a display 28 having a wrist strap 26 to hold the mobile unit 24 on a wrist of the anesthesiologist 20 so that the display 28 is easily viewable by the anesthesiologist 20 in the manner of a wristwatch. One or more user controls may be present on the exposed upper surface of the mobile unit 24 for access by the anesthesiologist 20 to control the display information on the display 28 and to provide other inputs from the anesthesiologist 20, for example, inputs indicating unavailability of the anesthesiologist 20 for providing limited control of the automatic anesthetic pump 10. As will be discussed, the mobile unit 24 may provide for alarm capabilities either in the form of an audible alarm, a flashing light, vibration, or a combination of these features.

Figure 3:
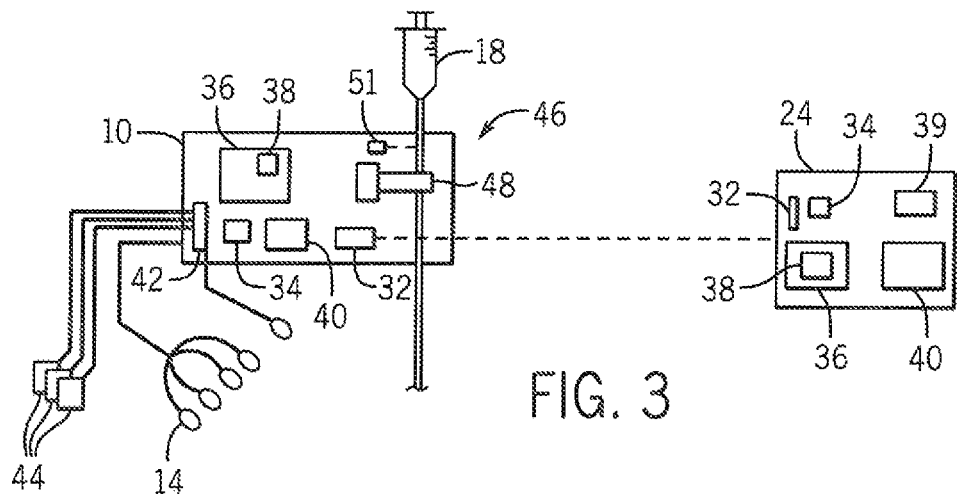
FIG. 3 is a hardware block diagram of the pump and remote monitor in one embodiment.

Referring now to FIG. 3, both the mobile unit 24 and the automatic anesthetic pump 10 may provide for wireless communication transceivers 32 either communicating directly with each other or indirectly through the wireless access points 22 (shown in FIG. 1). In addition, these devices may each include processors 34 communicating with memory 36 which may hold stored programs 38 implementing the present invention. A user interface 40 on each device allows for the display of information and the input of information from a user. On the mobile unit 24, the user interface 40 includes the display 28 and the user controls 30. The mobile unit 24 may include one or more alarm, elements 39, for example, a piezoelectric buzzer, a flashing light, or vibration motor for signaling the anesthesiologist 20. The wireless communication transceiver 32 on the pump 10 may further provide for communication with a remote rule server (not shown) that may hold current clinical rules providing best practice for the delivery of anesthesia. During the control process provided by the pump 10, these clinical rules may guide that control. The clinical rules may be held in the memory 36 and be upgradable, for example, by physical media attached to the pump 10 or over a network through the wireless connection or a wired connection. Alternatively, the clinical rules may be accessed in real time from a remote rule server which may assist in the control process.

The automatic anesthetic pump 10 also provides a physiological signal interface circuit 42 receiving inputs from the EEG electrodes 14 and the other physiological sensors 44 including respiration, blood oxygen, pulse, and the like. The physiological signal interface circuit 42 also provides output to the earphone 47 for providing instructions to the patient as has been discussed.

Importantly, the automatic anesthetic pump 10 includes a pump mechanism 46 for controlling delivery of the anesthetic 18, for example, Propofol, Etomidate, Barbiturates, and the like using a peristaltic pump element 48. The automatic anesthetic pump 10 may further include sensors 51 such as obstruction sensors, flow sensors, and the like, communicating with the processor 34 and indicating whether the intravenous line to the patient 12 is operating properly. Pump mechanisms of this type and suitable for this purpose are described in U.S. Pat. Nos. 8,652,093 and 8,945,043 assigned to the assignee of the present application and hereby incorporated by reference.

Figure 4:
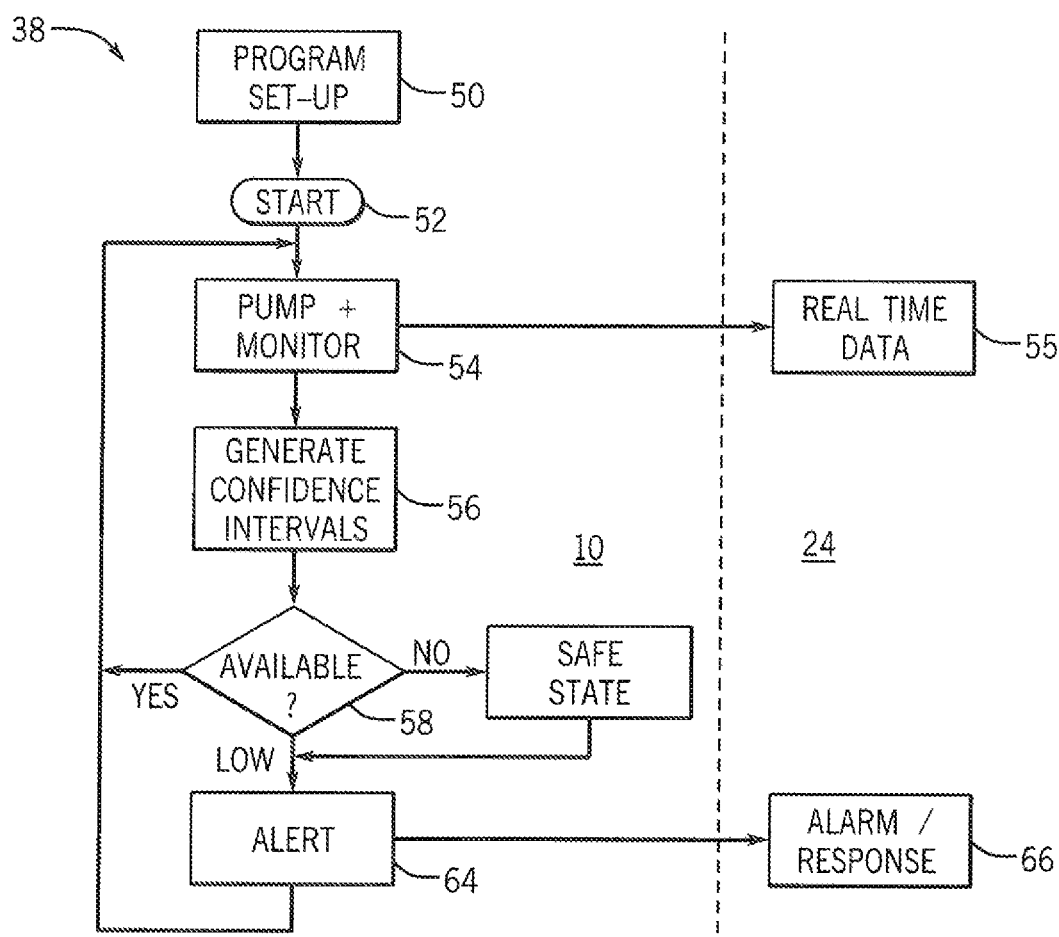
FIG. 4 flowchart of a program executed, by the pump of FIG. 3.

Referring now to FIG. 4, program 38 in the automatic anesthetic pump 10 may receive set up commands as indicated by process block 50, for example, identifying the patient weight and name and confirming the installation and operation of the various physiological sensors 44 and the EEG electrodes 14. This setup can be conducted through either of the user interfaces 40 of the automatic anesthetic pump 10 or the mobile unit 24.

Once the automatic anesthetic pump 10 is configured delivery of anesthetic may be started as indicated by process block 52. This starting process may require the presence of the anesthesiologist 20 at the bedside either by requiring an input to the automatic anesthetic pump 10 itself or by measuring the proximity of the anesthesiologist 20 using the mobile unit 24.

Once started, the automatic anesthetic pump 10 begins the delivery of anesthetic as indicated by process block 54. During this delivery, the physiological signals of the patient 12 are monitored and used to control the pump elements 48 (shown in FIG. 3) to produce a desired anesthesiology level in a closed-loop process. Techniques for monitoring and providing control of this type are described in the above-cited patents hereby incorporated in their entirety by reference.

During the monitoring of process block 54, data will be transmitted to the anesthesiologist 20 through the mobile unit 24 for on-demand viewing by the anesthesiologist 20 as indicated by process block 55.

At process block 56, the monitored data and operation of the pump in delivering anesthetic may be analyzed and the delivery process assigned to a confidence interval. The confidence interval may provide an analysis of whether the data represents a normal anesthesiology session, for example, by comparing it to historical data either using ranges or supervised machine learning or the like. Alternatively, the confidence interval may be an analysis of the brain state of the patient 12 with respect to the desired level of anesthesia. Confidence intervals of this latter type are described, for example, in patent 2014/0180160 incorporated by reference. The confidence level may optionally incorporate both of these elements and/or internal diagnostics indicating proper operation of the automatic anesthetic pump 10.

A high confidence interval will generally indicate that the automatic anesthetic pump 10 is performing properly and that there is no particular concern that requires close monitoring by the anesthesiologist 20. To the contrary, a low confidence interval generally indicates that attention by the anesthesiologist is required, not necessarily because there is a problem but possibly because the data is unfamiliar in some respect. At the lowest confidence interval levels, however, an error may be indicated or significant problems with the anesthesiology procedure that requires review by the anesthesiologist 20.

At decision block 58, the confidence interval may be compared against an anesthesiologist availability assessment by the automatic anesthetic pump 10 assessing a current or predicted availability of the anesthesiologist 20. This availability assessment may be a combination of the distance between the automatic anesthetic pump 10 and the mobile unit 24 (indicating physical distance separating the anesthesiologist 20 from the patient 12), a most recent viewing of data on the mobile unit 24 by the anesthesiologist 20, and/or possible instructions by the anesthesiologist 20 entered through the mobile unit 24 indicating a lack of availability, for example, as a result of an emergency or the like.

Figure 5:
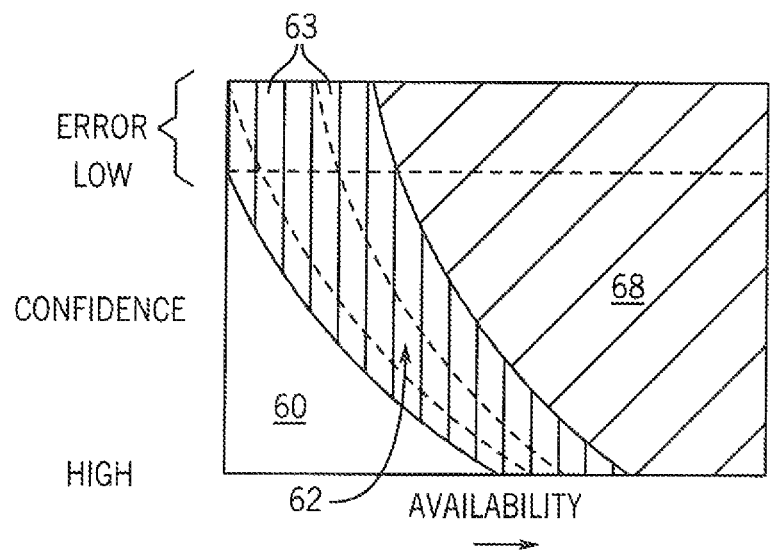
FIG. 5 is an example plot of confidence versus availability showing alarm and safe state levels used to provide tailored alerts to the anesthesiologist.

Referring also to FIG. 5, a combination of availability and confidence intervals may be used to define status zones guiding operation of the automatic anesthetic pump 10. A first status zone 60 is generally associated with normal operation of the automatic anesthetic pump 10 in which the patient 12 is continually monitored and anesthetic levels controlled while data is sent to the mobile unit 24. This first status zone 60 embraces both cases of low availability of the anesthesiologist 20 but high confidence in the operation of the automatic anesthetic pump 10 in controlling the anesthetic, and cases of lower confidence but high availability of the anesthesiologist 20, for example, when the anesthesiologist 20 is at bedside.

Further rightward from status zone 60 is status zone 62 which encompasses all error conditions and regions, to the right of status zone 60 where the availability of the anesthesiologist 20 is lower for each confidence level. Error conditions include internal diagnostics performed by the automatic anesthetic pump 10 including proper flow of anesthetic 18 as determined by sensors 51 which may determine obstruction and proper flow rate and proper operation of the internal electronics of the automatic anesthetic pump 10, for example, using processor watchdogs and checksums on memory values and program instructions known in the art. In this status zone 62, the anesthesiologist 20 will be given an alert either audible, visual, or tactile, indicating that immediate attention should be given to this patient and the automatic anesthetic pump 10 as indicated by process blocks 64 and 66.

At process black 66, the mobile unit 24 may provide a range of different instructions to the anesthesiologist 20 as determined by sub zones 63 within status zone 62, for example, to provide a response using user controls 30 confirming availability of the anesthesiologist 20 at a leftmost sub zone 63 or requesting that the anesthesiologist 20 return to the bedside, for example, at the rightmost sub zone 63. If a response is not received, the availability of the anesthesiologist 20 may be predetermined to provide a decreased assessment of availability which in turn may trigger additional actions by the automatic anesthetic pump 10.

If the confidence interval is sufficiently low and/or the availability of the anesthesiologist 20 is sufficiently low, a status zone 68 may be entered to the right of status zone 62. Entry into this status zone 68 is immediately transmitted to the mobile unit 24 with appropriate alerts and the automatic anesthetic pump 10 begins the process of moving the automatic anesthetic pump 10 into a safe state. A safe state may be defined for each procedure and drug type and does not necessarily involve shutting down the delivery of anesthesia although this is one option. In another option, the anesthetic level is reduced and additional alerts generated, for example, communicating with other hospital personnel or the like through the wireless access points 22. An alarm may also sound on the automatic anesthetic pump 10 to alert other attending medical personnel.

Figure 6:
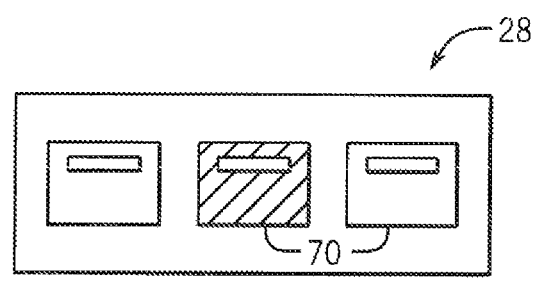
FIG. 6 is an example display of the remote monitor of FIG. 2 showing its capabilities for allowing monitoring of multiple anesthesiology pumps.

Referring now to FIG. 6, the display 28 of the remote device 24 may allow for simultaneous monitoring of multiple automatic anesthesiology delivery devices 10, for example, each represented by an icon 70. In one embodiment the icons 70 may each have a color indicating the status zones 60, 62 and 68 in which the respective automatic anesthetic pump 10 is operating and displaying important data necessary for the anesthesiologist 20. This displayed data may depend on the context, for example, displaying pulse rate and oxygen for automatic anesthesiology delivery devices 10 in status zone 60, but for status zone 62 and 68 displaying aberrant sensor data or the like as appropriately indicated.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as, necessarily requiring their performance in the particular order discussed or illustrated, unless specifically identified as an order of performance. It is also to be understood, that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

As used herein programming or data entry refers not only to adding data but modifying or deleting data in electronic memory.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A system for automatic delivery of general anesthetics based on patient monitoring comprising:
at least two independent pump units each including a processor executing a program stored in memory to receive physiological signals selected from a group consisting of blood oxygen, respiration rate, heart rate and brain waves from a corresponding patient under anesthesia and to provide a controlled delivery of drugs providing a reduced level of consciousness to the patient in an anesthesiology procedure in response to the received physiological signals, each independent pump unit further assessing a confidence interval assessing a degree to which the controlled delivery of drugs represents a normal anesthesiology session; and
a mobile unit communicating wirelessly with the at least two pump units concurrently to provide real time information to a remote anesthesiologist indicating a status of each anesthesiology procedure based on the received physiological signals and to provide information to the remote anesthesiologist associating the status with the patient and to provide alerts to the remote anesthesiologist indicating that immediate attention should be given to the patient based on the received physiological signals;
wherein each independent pump unit further assesses an availability of the anesthesiologist based on communication with the mobile unit; and
wherein the alerts to the remote anesthesiologist are dependent on a combination of both assessed availability and assessed confidence interval so that an alert is first provided (i) when the anesthesiologist is at a first distance when there is low confidence and (ii) when the anesthesiologist is at a second distance when there is high confidence, so that a decreased confidence interval triggers an alert at closer distances and an increased confidence interval triggers an alert at farther distances, where the anesthesiologist is closer to the pump unit at the first distance than at the second distance;
wherein the confidence interval is independent of the availability of the anesthesiologist.

2. The system of claim 1 wherein the mobile unit is sized and communicates with the pump unit so that it may be carried by the anesthesiologist.

3. The system of claim 2 wherein the mobile unit includes a wrist strap for holding on an anesthesiologist's arm in a manner of a wristwatch.

4. The system of claim 2 wherein the mobile unit provides a display indicating values of at least two physiological signals.

5. The system of claim 4 wherein the mobile unit provides a display indicating a qualitative status of the anesthesiology procedure.

6. The system of claim 5 wherein the qualitative status is indicated by a color of an icon representing the pump unit.

7. The system of claim 5 wherein the pump unit further provides signals to the mobile unit generating alerts selected from a group of visual, audible, or tactile alerts due to a change in the confidence interval.

8. The system of claim 7 wherein the mobile unit provides a display indicating a current confidence interval.

9. The system of claim 8 wherein the confidence interval is indicated by a color of an icon representing the pump unit.

10. The system of claim 1 wherein the pump unit determines availability of the anesthesiologist at least in part by an assessed distance between the pump unit and the anesthesiologist.

11. The system of claim 10 wherein the assessed distance is determined using wireless signals from the pump unit and mobile unit.

12. The system of claim 10 wherein the pump unit determines availability of the anesthesiologist at least in part by a self-reporting of availability by the anesthesiologist.

13. The system of claim 12 wherein the pump unit determines availability of the anesthesiologist at least in part by interaction by the anesthesiologist and the remote device for reviewing data on the remote device.

14. The system of claim 1 wherein the pump unit provides internal diagnostics for operation of the pump unit and wherein the alerts are also a function of an indication of failure of the pump unit.

15. The system of claim 14 wherein the failure is selected from a group consisting of failure of desired flow rate of anesthesia and failure of processor or memory.

16. The system of claim 1 wherein the processor executing the program stored in memory provides the controlled delivery of anesthesia to the patient by applying the physiological signals according to clinical rules.

17. The system of claim 16 wherein the clinical rules are stored in the memory and further including a communication channel for upgrading the clinical rules stored in the memory.

18. The system of claim 16 wherein the clinical rules are obtained in real-time.

* * * * *